US005792617A

United States Patent [19]

Rotman

[11] Patent Number: 5,792,617
[45] Date of Patent: *Aug. 11, 1998

[54] CELL PROLIFERATION-BASED AMPLIFIED DETECTION OF ANALYTES

[76] Inventor: M. Boris Rotman, 1062 E. Shore Rd., Jamestown, R.I. 02835

[*] Notice: The term of this patent shall not extend beyond the expiration date of Pat. No. 5,472,846.

[21] Appl. No.: 476,229

[22] Filed: Jun. 7, 1995

Related U.S. Application Data

[63] Continuation-in-part of Ser. No. 292,416, Aug. 17, 1994, Pat. No. 5,472,846.

[51] Int. Cl.$^6$ .................................................. G01N 33/574
[52] U.S. Cl. .................... 435/7.23; 435/5; 435/6; 435/7.1; 435/7.2; 435/7.5; 435/7.9; 435/29; 435/34; 435/839; 435/834; 435/848; 435/878; 435/881; 435/883; 435/966; 436/527; 436/531; 436/807; 436/808; 436/813
[58] Field of Search .................... 435/5, 6, 7.1, 7.2, 435/7.23, 7.5, 7.9, 7.91, 7.92, 29, 34, 839, 834, 848, 878, 881, 883, 966; 436/527, 531, 807, 808, 813

[56] References Cited

U.S. PATENT DOCUMENTS

| | | | |
|---|---|---|---|
| 4,563,417 | 1/1986 | Albarella et al. | 435/6 |
| 4,665,018 | 5/1987 | Vold | 435/6 |
| 4,670,382 | 6/1987 | Buckley et al. | 435/7.9 |
| 4,880,731 | 11/1989 | Kaspar et al. | 435/7.9 |
| 5,194,382 | 3/1993 | Herrmann et al. | 435/207 |
| 5,244,785 | 9/1993 | Loor et al. | 435/5 |
| 5,306,468 | 4/1994 | Anderson et al. | 422/101 |
| 5,385,822 | 1/1995 | Melnicoff et al. | 435/5 |
| 5,472,846 | 12/1995 | Rotman | 435/7.9 |

OTHER PUBLICATIONS

Hunter and Bottenstein, "Growth Factor Responses of Enriched Bipotential Glial Progenitors," 54, *Developmental Brain Research* (Amsterdam, the Netherlands) pp. 235–248 (1990).

Rotman and Cox, "Specific Detection of Antigen-Binding Cells by Localized Growth of Bacteria," 68, *Proc. Nat. Acad. Sci.* (Washington, D.C.) pp. 2377–2380 (Oct. 1971).

Wilchek and Bayer, "The Avidin-Biotin Complex in Bioanalytical Applications," 171, *Analytical Biochemistry* (San Diego, CA) pp. 1–32 (May 1988).

*Primary Examiner*—Carol A. Spiegel
*Attorney, Agent, or Firm*—David Knaack

[57] ABSTRACT

A test kit and method for the highly sensitive detection of specific analytes in a sample is provided. The presence of the analyte in the sample results in a decrease in the concentration of a growth inhibiting substance leading to proliferation of cells in the region of the analyte. The presence or absence of the analyte is determined by detecting the presence of increased numbers of cells. Assay sensitivity is accounted for by the exponential amplification of cell number that occurs during cell proliferation in the presence of analyte.

17 Claims, No Drawings

CELL PROLIFERATION-BASED AMPLIFIED DETECTION OF ANALYTES

This application is a continuation in part of application U.S. Ser. No. 08/292,416, issued U.S. Pat. No. 5,472,846, filed on Aug. 17, 1994, entitled Test Kit and Method for Amplification and Detection of Antigen Cells.

BACKGROUND OF THE INVENTION

Highly sensitive detection systems have become important analytical tools in medical diagnostics and biological research, as illustrated by the use of fluorescence immunochemistry, flow cytometry, enzyme-linked immunocytochemistry, and in situ DNA and RNA hybridization. In some areas, nevertheless, there is a substantial interest in developing new cost-effective techniques which extend presently available detection limits. For example, some patients with early-stage cancer have small number of metastatic tumor cells in their bone marrow which escape detection by routine procedures such as bone scan, biochemical analysis, and cytological examinations. The most frequently used methodology for detecting these rare tumor cells, usually referred as occult micrometastases, is immunocytochemistry (Premi, T., and Battifora, H. Human Pathol. 18, 728–734, 1987, hereby incorporated by reference). At present, however, immunocytochemistry cannot be used on a routine basis because it is extremely labor-intensive. For example, a histopathology-trained technician requires about four hours of microscopic scanning to analyze a specimen (and appropriate controls) containing less than 10 malignant cells per million bone marrow cells.

Automated screening techniques, such as flow cytometry and computerized image analysis, not only require extensive capital investments but have been found to be less sensitive than conventional immunocytochemistry. It is clear, therefore, that in this particular field there is a need for simple and cost-effective techniques capable of detecting malignant cells present at low frequencies in clinical specimens of blood or bone marrow. Other clinical fields may also benefit from such techniques because, for example, they could provide sensitive means to: 1) detect early relapse in cancer patients; 2) test effectiveness of adjuvant treatments throughout therapy of patients with metastastic disease; 3) monitor the presence of tumor cells in blood or bone marrow used for autologous transplantation to prevent infusion of tumor cells into patients; 4) track circulating genetically engineered cells in patients. Similarly, simple, more sensitive techniques could aid clinical and investigational applications for lowering the detection levels of histologically important macromolecules which are presently analyzed using enzyme linked or radioactive probes. For example, amplification-visualization techniques currently used for DNA probe detection include enzyme-catalyzed reactions yielding chemiluminescent products, fluorescent products, or colored insoluble precipitates. Typically, in these techniques, a labeled nucleic acid probe is annealed to a complementary DNA or RNA target sequence which is either in solution or immobilized on an inert support. The binding of the labeled probe (usually an oligonucleotide which either contains a radioactive element or is attached to an enzyme via conventional ligand-binding protein technology) reports the presence or absence of a the target sequence in the reaction mixture. Examples of clinical applications using DNA probe amplification visualization are tests for viruses, oncogenes, or multiple resistance genes using enzyme-labeled DNA probes.

SUMMARY OF THE INVENTION

The invention relates to a test kit and a method for the detection of target molecules and analytes through the use of bimolecular probes which bind to the target molecules.

The underlying basis of the invention is the bacterial chain reaction (BCR), an innovative amplification-visualization system. The BCR utilizes living cells to detect an analyte. The inventive method described herein is useful for the determination of an analyte in a sample. The method involves providing a sample comprising the analyte and complexing the analyte with a multifunctional probe said probe comprising a binding domain and a growth promoting activity domain to form a multifunctional probe-analyte complex, wherein said growth promoting activity is capable of acting on a preselected regulatory substrate to promote the growth of proliferative cells. The multifunctional probe-analyte complex is then contacted with a reaction matrix comprising (i) the regulatory substrate and (ii) a sample of the proliferative cells whose growth is enhanced by the activity of the multifunctional probe on the regulatory substrate. The entire sample is then incubated for a time sufficient to provide the production of a growth promoting environment and the growth of the proliferative cells.

The analyte is then detected by observing the occurrence of new proliferative cells.

In one embodiment the analyte is a cell surface antigen. In other embodiments the analyte is located within a cell which is permeabilized. In some instances the analyte may be present on a blot. In a preferred embodiment, the analyte is a known marker for mammalian tumor cells. In still other embodiments, the analyte will be present in a sample of blood or bone marrow. In some embodiments the analyte is a protein or a nucleic acid.

The inventive method may employ a multifunctional probe which comprises enzymatic activity selected from the group consisting of β-lactamase, β-galactosidase, glucosidase, esterase, acetyltransferase, adenyltransferase, adenosine deaminase, penicillinase, nucleosidase, and phosphotransferase.

In preferred embodiments the regulatory substrate is an antibiotic selected from the group consisting of cephalosporins, chloramphenicol, kanamycin, formycin, penicillins, puromycin, streptomycin, and gentamycin.

In the most preferred embodiments the proliferative cells are bacteria. A preferred bacterium for use in the BCR may be selected from the group consisting of *Bacillus subtilis, Bacillus cereus, Escherichia cloacae, Providencia stuartii, Pseudomonas aeruginosa, Serratia marcescens, Sarcina lutea, Vibrio fischeri, Escherichia coli,* and *Staphylococcus aureus.*

In one specific embodiment, the probe comprises a murine IgG monoclonal antibody and the enzymatic activity is indirectly conjugated thereto through antimouse IgG antibody. In another preferred embodiment, the analyte is cytokeratin and the probe comprises anticytokeratin immunoreactivity.

In another embodiment, enzyme-labeled monoclonal antibodies directed against particular tumor antigens may be used to detect and quantify specific tumor cells bearing the particular antigens. Under appropriate conditions, the antigen bearing tumor cell coated with enzyme linked probe molecules triggers nearby bacterial cells to initiate proliferation resulting in a visible cluster of bacterial micro colonies (termed here "satellite colony") surrounding the tumor cell. Thus, the amplification effected by the BCR has considerable practical importance because it is naturally coupled to visual signals (i.e., satellite colonies) reporting the presence of rare tumor cells bearing the particular antigen in a large population of normal cells. In this particular example, it is possible to obtain quantitative estimates of the rare cells (i.e., antibody-binding cells present in the analyte) by simply enumerating satellite colonies.

The invention includes a test kit useful to carry out this method, which test kit comprises an enzyme-conjugated multifunctional probe molecule adapted to react with the analyte to form analyte-probe-complex molecules; a solid reaction matrix-coated surface which coated surface comprises a selected antibiotic adapted to be destroyed by the enzymatic activity of the multifunctional probe and selected antibiotic-sensitive bacteria cells whereby the coated surface is exposed to the multifunctional probe and incubated to form a satellite colony of bacteria micro colonies which are then detected.

The analyte (typically a suspension of human or animal cells containing a very small percentage (e.g., 0.001%) of probe-specific cells) is treated so as to coat the specific cells with reporter molecules suitable for the BCR. For example, a cellular analyte is sequentially treated with specific monoclonal antibodies and a covalent conjugate of β-lactamase I and antimouse IgG or IgM immunoglobulin. These conjugates can be obtained by a variety of methodologies, and the immunoglobulin is usually produced in animal species other than mouse, e.g., rabbit, goat, guinea pig or horse. Between each of the treatments, the analyte is washed several times with phosphate-buffered saline (PBS) containing 1% bovine serum albumin (BSA). As a result of these treatments, probe-specific cells (in contrast to all other cells in the analyte) acquire a coat of β-lactamase I. At this stage, a sample of the analyte is added to melted soft agar (kept at 45° C.) containing penicillin V (a substrate hydrolyzed by β-lactamase I, and also an inducer of β-lactamase I synthesis in some bacterial species), and cells of a penicillin-sensitive bacterium carrying an inducible β-lactamase I operon or a penicillin-sensitive bacteria genetically engineered to carry an inducible β-lactamase I operon. Under the conditions indicated above, probe-specific cells are detectable because their newly acquired enzyme coating hydrolyzes antibiotic in the immediate vicinity of the probe-specific cell triggering a proliferative chain reaction among nearby bacteria.

The BCR is the result of several interconnected events, some predictable others unexpected. For the given example, these events are: i) the penicillin concentration near a β-lactamase I-coated cell is drastically lowered because of enzymatic degradation; ii) as the local penicillin concentration falls below certain threshold, bacteria in the vicinity of individual β-lactamase I-coated cells start proliferating; iii) proliferating cells, in contrast to stationary bacterial cells, are induced by penicillin to produce β-lactamases; iv) bacteria synthesizing β-lactamases become less sensitive to penicillin; v) local penicillin concentration is further lowered by the bacterial enzymes; vi) further cycles of bacterial proliferation and induction occur. The overall result (after several hours of incubation) is formation of a satellite colony surrounding the probe-specific cells present in the analyte. A satellite colony typically consists of 5–100 bacterial microcolonies of different sizes (range 0.1–2.0 mm) arranged in a circular pattern with large microcolonies located near the center of the satellite colony, and proportionally smaller microcolonies towards the periphery. This characteristic morphology of a satellite colony (which is independent of overall colony dimension and number of microcolonies within the satellite colony) results from a concentration gradient of antibiotic causing rapid proliferation of bacteria near an enzyme-coated cell, as compared to bacteria further away from the cell. The morphology plays an important role in the BCR assay because bacterial contaminations do not interfere with the assay since they grow as single colonies, i.e., they do not produce satellite colonies.

In another embodiment of the invention, probe-specific cells to be analyzed are present in cell populations (or tissue sections) fixed on a surface such as a microscope slide. This type of analyte presentation is often encountered when clinical specimens, such as bone marrow or circulating leukocytes, are used for histopathological or immunocytochemical examinations. As in the previous embodiment, the cells are treated so as to coat them with an enzyme suitable for the BCR. In this case, however, the treatment is applied by sequentially dipping the slides in reagent solutions. After treatment, the slides are covered with a thin layer of melted soft agar containing antibiotic and bacteria. After a few hours of incubation, satellite colonies appear at discrete locations around probe-specific cells. After marking the location of the satellite colonies on the slide and removing the soft agar layer, the results of the BCR assay can be directly verified by conventional cytochemical techniques. For example, the slide may be counterstained with a fluorescence-labeled monoclonal antibody to ascertain the specificity of the cells reported by satellite colonies. Alternatively, the reported cells can be scraped off, and analyzed for specific DNA or RNA sequences using the polymerase chain reaction.

In a different embodiment of the invention, the analyte is immobilized on a matrix such as a membrane filter. This type of analyte presentation is often encountered during analytical separation of proteins, nucleic acids and other macromolecules by electrophoresis. As in previous embodiments, the matrix is treated with reagents designed to specifically coat the analyte with a suitable enzyme. Subsequently, the matrix is covered with a thin layer of melted soft agar containing antibiotic and bacteria. After a few hours of incubation, satellite bacterial colonies mark the analyte location on the matrix.

PREFERRED EMBODIMENTS

The present invention features high sensitivity assays for a variety of analytes employing the BCR system to amplify and detect probes bound to analytes. The invention comprises detection of an analyte through the use of a specific analyte-binding probe. The probe is multifunctional, being capable of binding to the analyte as well as possessing activity which is capable of producing a change in the environment surrounding the analyte. The changed environment is conducive to cell growth. The analyte is detected by placing the analyte-probe conjugate in the presence of cells such as bacteria, the growth of which is allowed or promoted in the vicinity of the probe due to the growth-promoting activity comprised by the multifunctional probe. The end point is cell proliferation which can potentially be used to determined the presence, location, and/or number of specific analyte-bound probes.

Analytes

The present invention is designed to detect the presence, and in some cases the quantity of specific target analytes. As used herein the term "analyte" is meant to refer to the target macromolecules to be detected. It is an important aspect of the invention that the target macromolecule be accessible, or made accessible at some point, to bind analyte-specific probes of the instant invention.

In most cases the analyte will be insoluble or easily immobilized. As indicated above, the analyte may be present and accessible on the surface of cells, it may also be present on a blot. As used herein "blot" refers to any number of methods which results in the immobilization of a macromolecule on filter paper, nitrocellulose, nylon or other blotting materials such as are used in slot or dot blots, Northern, Western and Southern blots.

Illustrative examples of useful analytes include, but are not limited to, the following: 1) specific cell surface macromolecules and antigens (including hormones, protein complexes, and molecules recognized by cell receptors) 2) cellular proteins, DNA or RNA in permeablized cells including abnormal DNA or RNA sequences or abnormal amounts of certain messenger RNA. Detection of these analytes is particularly useful in situations where they are contained in and/or are identifiers of rare cells such as are found in the early stages of a variety of cancers. In some embodiments the analyte will be a soluble macromolecule.

Analyte-binding probes

As defined herein, an analyte binding probe or "probe" comprises molecules capable of specifically binding, complexing, associating or otherwise adhering to the analyte (hereafter referred to as "binding" the analyte). Examples of analyte-binding probes comprising proteinaceous substances (such as glycoproteins, lipoproteins, and others) include specific immunoreactive molecules (e.g. polyclonal antibodies, monoclonal antibodies and fragments thereof), specific binding proteins (such as biotin-binding protein (avidin, streptavidin) carbohydrate binding protein (lectins) and RNA or DNA binding proteins), cell receptors, receptor agonists, and transport proteins but not limited to these examples. Examples of analyte-binding probes comprising nucleic acids include natural or synthesized oligonucleotides complementary to sequences present in tissues of human, animal or plant origin, viruses, bacteria, plasmids, and in genetically engineered organisms or man-made constructs.

In some instances the probe will also contain a hapten, or other component capable of binding to a secondary multifuctional probe (see below). In specific preferred embodiments when the analyte is a nucleic acid the probe may be haptenized DNA (e.g. biotinylated).

Multifunctional probes

As used herein "multifunctional probe" refers to a molecule or conjugate or complex of molecules, which contains a "binding domain" and a "growth-promoting activity" domain. The purpose of the multifunctional probe is to juxtapose a growth-promoting activity with the analyte, thereby establishing a growth-promoting activity in the region of the analyte which will subsequently be detected by the growth of the proliferating cells.

In preferred embodiments the binding domain of the multifunctional probe will be an analyte-binding probe as described above. In the special case where the binding domain of the multifunctional probe is meant to bind to another distinct analyte-binding probe, the multifunctional probe is referred to as a "secondary multifunctional probe" and the other analyte-binding probe is called the "primary probe" In either case, once the multifunctional probe is complexed to the analyte with or without an intermediate primary analyte-binding probe, the complex is referred to as an "analyte-multifunctional probe complex".

The growth promoting activity of the multifunctional probe may be any species or substance capable of establishing a growth promoting environment near the analyte. In most cases the activity is an enzyme or catalyst, although radioactive, luminescent and other active molecules are also contemplated.

In preferred embodiments the multifunctional probe employs an enzymatic growth-promoting activity conjugated to an analyte-binding probe. Enzyme-probe conjugates can be prepared by a large variety of methods which preserve the specificity and sensitivity of the particular probe as well as the catalytic activity of the enzyme. Preferred embodiments of this invention utilize enzyme labeled probes prepared by covalent conjugation with glutaraldehyde as described in U.S. Pat. No. 4,002,532, January 1977, hereby incorporated as a reference. Alternatively, enzymes can be directly conjugated to probes using one of the many methods described in the literature.

Secondary multifunctional probes employ indirect procedures for obtaining stable probe-analyte complexes. These procedures are generally based on ligand-binding technology such as that developed for biotin-avidin or digoxigenin-antidigoxigenin antibody. For example, an enzyme-streptavidin conjugate provides an intermediate to label proteinaceous probes containing biotin since streptavidin binds biotin with a high association constant. Biotin-containing probes can be easily synthesized by well known methods or in many instances are commercially available. Examples of biotin-labeled and digoxigenin-labeled probes include antibodies (polyclonal, monoclonal, or fragments thereof), oligonucleotides, lectins and binding proteins. This method is specially useful for enzyme-labeling oligonucleotide probes synthesized with biotin-labeled or digoxigenin-labeled nucleic acid precursors.

In preferred embodiments useful for identifying nucleic acid analytes, the primary probe is a nucleic acid conjugated to a hapten (e.g. biotin), and the secondary multifunctional probe is an antibody-enzyme complex. The instant invention also contemplates more complex indirect labeling procedures employing "sandwiches" of multiple probes.

Proliferative cells (e.g. Bacteria)

The proliferative cells present in the invention proliferate in the vicinity of the analyte in response to the establishment of a growth promoting environment by the multifunctional probe. The proliferation of the cells then, indicates the presence, location and/or quantity of analyte.

Due to their rapid proliferative rate, bacteria are the most preferred organisms of the instant invention. Other organisms such as yeast, algae or various eukaryotic cell lines and preparations (e.g. plant or insect-derived cells, some of which have doubling times less than 10 minutes) may potentially be used in place of bacteria in this reaction. The use of slowly dividing cells will diminish much of the power of the instant invention. In general, organisms with doubling times of less than 30 minutes are preferred. More rapid doubling times such as those found in *E. coli* and *S. lutea* are most preferred. In addition to rapid proliferative rate, it is preferred that the organism to be employed in the BCR reaction be compatible with growth on or in a useful reaction matrix and that a suitable antibiotic or other growth inhibitory substance be available. In preferred embodiments the inhibitory substances retards or stops proliferative cell growth without actually killing the cells.

Either vegetative bacterial cells or spores may be used for the BCR assay. For example, *Sarcina lutea* cells are grown in Difco Heart Infusion broth at 37° C. Cultures are aerated in a tube roller, and harvested before reaching stationary phase. It should be noted that cryopreserved cultures may be used for the BCR assay. For cryopreservation, the cultures are mixed with glycerol (20% final concentration), divided in aliquots, and placed at −20° C. When using spores, cultures are allowed to reach stationary phase under conditions leading to sporulation. Spores are collected by centrifugation, washed in distilled water, and heated at 65° C. for 30 minutes. After heat treatment, spores are washed three times with distilled water and the heating step is repeated. Spore suspensions can be maintained at 0°–4° C. for several weeks. The following represent examples of bacterial strains useful with the BCR (but not limited to these): *Bacillus subtilis, Bacillus cereus, Escherichia* cloacae, Providencia stuartii, Pseudomonas aeruginosa, Serratia marcescens, Sarcina lutea, Vibrio fischeri, Escherichia coli, and Staphylococcus aureus.

Growth Regulation Systems

It is an important feature of the invention that the multifunctional probe has the capability of promoting cell growth. Thus it will be important that the activity of the growth promoting domain of the multifunctional probe and the cell growth regulating agent to be modified by the multifunctional probe, be closely matched with the cells to be used for detection. As used herein growth regulation system refers to the system comprising the proliferative cells, the growth promoting activity present on the multifunctional probe, and the substrate on which the enzyme acts (herein called the regulatory substrate) to produce a growth promoting environment. In preferred embodiments the growth regulation system will comprise an antibiotic, an antibiotic degrading enzyme and a specific bacterial strain. In this case, the regulatory substrate is the antibiotic. However, the current invention also contemplates the use of other growth enhancement strategies such as would occur with an auxotrophic bacterial strain when the enzymatic activity of the multifunctional probe is intended to produce the auxotrophic amino acid from a precursor present in the growth medium.

In the case of antibiotic dependent embodiments, the prerequisites for using a particular enzyme-antibiotic combination for the BCR are: (1) the antibiotic has to be either cytotoxic or cytostatic for the particular species of bacteria used in the system, and (2) the enzyme present on the multifunctional probe has to alter the activity of the antibiotic enough to allow cell growth. Most often this will be complete destruction of the antibiotic activity. Examples of enzyme-antibiotic combinations suitable for the BCR (but not limited to these examples) are shown in Table 1.

TABLE 1

Examples of enzyme-antibiotic combinations suitable for BCR

| Antibiotic(s) | Enzyme(s) |
| --- | --- |
| Cephalosporins | B-lactamases II |
| Chloramphenicol, kanamycin, | acetyltransferases, adenylyltransferases |
| Formycin | adenosine deaminase |
| Penicillins | β-lactamases I, penicillinases |
| Puromycin | nucleosidases |
| Streptomycin, gentamycin | phosphotransferases |

It should be mentioned that for certain enzyme-antibiotic combinations it is possible to separate the antibiotic-destroying activity from the inducer activity. For example, a hybrid molecule consisting of cephalosporin (an antibiotic hydrolyzed by β-lactamase II) and isopropyl-β-D-galactoside (an inducer of the lac promoter) will liberate isopropyl-β-D-galactoside in the immediate surroundings of an analyte coated with β-lactamase II. Under these conditions, a bacterium carrying a lac promoter upstream of the β-lactamase II gene will begin to synthesize β-lactamase II in response to the inducer liberated near the analyte. This action, in turn, will increase local hydrolysis of cephalosporin-isopropyl-β-D-galactoside thus intensifying the BCR.

An example of a suitable auxotrophic system is the use of a proliferative cell comprising a bacterial strain auxotrophic for glutamic acid, a glutamate ester regulatory substrate and an esterase activity on the multifunctional probe.

Reaction matrix

The reaction matrix as used herein refers to the milieu containing the proliferative cells, growth medium for the proliferative cells, the regulatory substrate to be acted on by the growth promoting activity present in the multifunctional probe, and any three dimensional support structure to be employed to support the BCR. While the components of the reaction matrix may be configured in a variety of ways, the most important feature of the reaction matrix is that it maintains the probe-analyte complex in the presence of the proliferative cells and that it also provides the substrate on which the multifunctional probe can act to promote cell growth in the region of the probe. In the preferred embodiments the reaction matrix also maintains the probe-analyte complex in a fixed position relative to those proliferative cells the growth of which is being promoted. In most preferred embodiments, the matrix comprises an agar or other hydrogel such as alginate, agarose, collagen or hyaluronic acid. In most cases the proliferating cells will be uniformly distributed within the reaction matrix. In some embodiments, the probe-analyte complex is dispersed within the growth substratum. In other embodiments the probe-analyte complex will be present on a supporting matrix and the proliferating cells will be uniformly distributed within the reaction matrix which will be layered over the supporting matrix. In this embodiment, the reaction matrix may be applied as a solid hydrogel often times attached to glass or plastic, or applied as a liquid an allowed to "set up" following application.

Bacterial cells are generally present within the reaction matrix at a concentration of $10^4$–$10^8$ cells/ml.

Analyte samples

In many instances the target analyte will be on or in a specific cell. If the analyte is present on the cell surface, provided that a suitable probe is available, living cells comprising the cell surface analyte may be used in the assay. In many of the preferred embodiments, however, prior to initiation of the BCR, cells will be fixed with a fixative agent such as ethanol, acetone, or paraformaldehyde. If the analyte is present within the cell, the analyte must be made accessible to the probe either by means employing cell lysis, or through one of the permeabilization methods known to practitioners of immunocytochemistry.

In some embodiments, the analyte will be present as a soluble compound. From other samples, the analyte may be extracted and/or solubilized prior to use in the BCR. The sample containing soluble analyte may then be processed through any number of purification steps (such as extractions and column chromatography), or the sample may be used directly in the BCR provided there are no substances present in the sample which compete with or are otherwise deleterious to any of the processes important for the successful operation of the BCR. In any event, following binding of the analyte to the probe, excess probe must be eliminated in order to provide for a usable signal-to-noise ratio. In many of the preferred embodiments, the probe-analyte conjugate will be immobilized. In such cases, excess probe can then be removed with a series of washes. Useful immobilization methods include the use of a multifunctional probe bound to a support substance such as magnetic beads or filter paper prior to contacting the multifunctional probe with analyte. Secondary antibodies capable of recognizing analyte-probe conjugate may be used to immunopreciptate the analyte-probe conjugate. In the precipitated form, the conjugate may be washed and excess probe removed.

In a preferred embodiment, the sample containing analyte is subjected to electrophoresis on paper, polyacrylamide, agarose or other electrophoretic substrate. Following electrophoresis, the analyte is blotted from the electrophoretic substrate by methods known in the art. Whole, purified, or partially purified samples may also be fixed to blots using conventional slot and/or dot blot technologies. Following blot preparation, the multifunctional probe can be bound to the blot, and the blot is then rinsed with an appropriate number of washes. The BCR reaction is then initiated by exposing the blot to the reaction matrix containing the proliferative cells and regulatory substrate.

Alternatively, unbound multifunctional probe may be destroyed, trapped or otherwise removed from the reaction. In the case of nucleic acid probes unbound probe may be trapped with immobilized complementary nucleic acid sequences, or destroyed using approaches such as S1 nuclease digestion.

Detection

Detection of analyte in the BCR is accomplished by identification of regions within the reaction matrix that have increased numbers of proliferative cells as compared to the background levels existing elsewhere in the reaction matrix. Any method which allows such detection of cell proliferation over the background may be used. Many of the embodiments of the instant invention employ visual detection, either using the naked eye or through a microscope. Depending upon the magnification available the amount of incubation time can be varied. Detection can be enhanced through the use of fluorescent, pigmented, or luminescent proliferating cells. Non-limiting examples of useful such cells include naturally luminescent bacteria such as *Vibrio fischeri*, or cells genetically engineered to have such properties (e.g. through the introduction of the luciferase gene). β-Galactosidase containing species of proliferating cells may also be useful in some instances as they can be induced to produce a colored reaction product through the addition of chromogenic substrates.

Alternatively the signal may be enhanced through the incorporation of metabolic dyes into the growth substratum. Alamar blue is an example of one such dye. When using metabolic dyes, fluorescent or luminescent cells, it may be useful to employ a spectrophotometric or fluorometric microscope which can detect a specific wavelength of light associated with the metabolic dye. In one preferred embodiment where luminescent cells are employed, following completion of the BCR, a light sensitive film is juxtaposed to the reaction matrix. The film is left in the presence of the reaction matrix for a sufficient time to allow light emitted from the luminescent cells present in the reaction matrix to expose the film. The analyte is then detected by developing the film and looking for regions of exposure which are greater than the background level.

BCR Assay

The BCR assay comprises binding the analyte with the multifunctional probe either directly or indirectly through the use of a separate analyte-binding probe. Placing the multifunctional probe-analyte complex in the presence of the reaction matrix to form the BCR reaction system and incubating the BCR reaction system under appropriate conditions to achieve detectable growth of the proliferative cells. The correct incubation conditions are dependent upon the cells chosen as well as the other components of the assay system. Those practiced in the art of cell biology & microbiology will know the appropriate conditions (e.g. temperature, growth medium etc.) to promote cell growth of the particular proliferative cell. Additional guidance for optimization of the assay system can be found through the use of test systems which employ artificial analytes present on substances such as threads or beads. Suitable such assay systems are described in the examples below.

The components and reagents of the BCR assay system of the present invention may be supplied (in aqueous or lyophilized form) in the form of a kit in which the simplicity and sensitivity of the assay are preserved. All necessary reagents can be added in excess to accelerate the reactions. In preferred embodiments, the kit will comprise a sample holding means which will generally be in the form of a microscope slide or petri dish. In kits designed for detection of analytes in blots the sample holding means may consist simply of a tray in which to place the prepared blot. The kit also comprises a preformed reaction matrix in the form of a film, to be applied to a sample containing an analyte. The preformed reaction matrix will generally consist of a hydrogel matrix (e.g. agar) in which bacteria are dispersed in the presence of a bacteriostatic agent such as penicillin. The matrix may be attached to a backing means which will most often be a flat sheet like material made of a polymer (e.g. cellulose acetate or PVA) or glass. The backing means functions to provide mechanical strength and ease of handling to the reaction matrix. The matrix film may be applied directly on the sample containing analyte, and the backing may be left in place or removed as needed. In most embodiments, the backing material will be transparent to allow quantitation on a microscope, densitometer, fluorimeter or other apparatus. The exact apparatus to be employed for visualization will depend on the properties of the bacteria, and any particular signal enhancing methods employed in the kit.

In some embodiments the BCR is performed in situ. In these embodiments the cells to be analyzed may be first fixed on glass microscope slides or similar supports. The slides are then treated sequentially with probe followed by a multifunctional probe or by the multifunctional probe alone. Washings are then performed by submerging the slides in a wash solution such as PBS-BSA using any convenient container such as staining (Coplin) jars. Immediately following the final wash, the slides (cell side down) were placed on agar films containing the reaction matrix. After an appropriate incubation period suitable to cause adequate proliferative cell growth the location of satellite colonies is determined under a microscope or with the naked eye.

EXAMPLE 1

Enumeration of rare tumor cells in human bone marrow or blood specimens

This example illustrates a BCR assay for tumor cells present at extremely low frequency among normal bone marrow cells or peripheral blood leukocytes. To coat probe-specific cells with β-lactamase I, cells were treated sequentially with anticytokeratin monoclonal antibody specific for cytokeratin 18 (Sigma Chemical Co.) and a covalent conjugate of goat antimouse immunoglobulin (Sigma) and β-lactamase I (Sigma).

Preparation of analytes

Two-ml samples of blood or bone marrow specimens (collected with heparinized syringes) are diluted 1:2 with phosphate-buffered saline (PBS), and the nucleated cells are separated using Ficoll-Hypaque (Litton Bionetics, Inc.) density gradient centrifugation. After centrifugation, nucleated cells at the interface are collected, washed twice with PBS, resuspended in 0.5 ml PBS, and counted in a hemocytometer. Cellular viability is measured using fluorochromasia. Buffy coats from either blood or marrow specimens may be substituted for nucleated cells separated by density centrifugation. To this end, blood or bone marrow specimens are decanted for 10 min at room temperature, and the top layer containing mostly nucleated cells is separated. As before, cells are washed twice with PBS and counted. Typically, cell suspensions from buffy coats contain less than 10% red cells, an amount that does not interfere with the BCR assay. These observations are important because the invention can circumvent Ficoll-Hypaque separation, a costly, and time consuming step required for histology, immunocytochemistry and other methodologies.

Nucleated cells resuspended in PBS are fixed by adding an equal volume of ethanol under strong agitation (Vortex mixer), and letting the suspension incubate at room temperature for 30 minutes. The fixed cells are collected by centrifugation. Different monoclonal antibodies may require different fixation treatments. The fixed cells resuspended in PBS may be stored at 0°–4° C. for several days. Fixed cells can be kept in ethanol at –20° C. for several weeks.

Enzyme-probe covalent conjugates

Covalent conjugates were prepared following the procedure described in U.S. Pat. No. 4,002,532, Jan. 11, 1977, hereby incorporated as a reference. Fifty micrograms of goat antimouse IgG (whole molecule, adsorbed with human serum proteins, Sigma Chemical Co.) were conjugated with 410 micrograms of β-lactamase I (Sigma) in the presence of 0.02M glutaraldehyde. After 4 hours of incubation at room temperature, the reaction mixture was dialyzed extensively against PBS containing 0.05% sodium azide. The conjugate was separated from the reaction mixture using SEPHADEX™ G-200 chromatography.

BCR Assay

Suspensions of fixed cells were treated sequentially with specific monoclonal antibodies and enzyme-probe covalent conjugate. Between each treatment, the cells were washed twice with PBS-BSA. Typically, cells were treated with a dilution 1:100 of the anticytokeratin 18 monoclonal antibody for 30 min at room temperature, separated by centrifugation, and washed with PBS-BSA twice in the same manner. The cellular pellet was resuspended in a dilution (e.g., 1:500) of the enzyme-probe covalent conjugate, and incubated for 30 min at room temperature. After incubation, the cells were washed four times with PBS-BSA, and then added to 10 ml of melted soft agar (0.45% Difco heart infusion agar kept at 45° C.) containing penicillin V ($10^5$ units/ml) and $S.$ $lutea$ cells ($10^6$ cells/ml). After overnight incubation at 37° C., bacterial satellite colonies on the plate were counted using a dissecting microscope or a magnifying lens.

To test the specificity of the BCR assay, normal human nucleated cells from either blood or bone marrow were mixed with limiting numbers of cells from MCF-7, an established cell line originally isolated from a patient with metastatic mammary adenocarcinoma. Results showed that satellite colonies were present only on plates containing nucleated cells mixed with MCF-7 cells. In addition, controls missing either the monoclonal antibody or the antibody-enzyme complex did not have satellite colonies.

EXAMPLE 2

Enumeration of rare tumor cells in human bone marrow or blood specimens fixed on microscope slides This example illustrates the use of the invention for enumerating tumor cells present at extremely low frequency among normal bone marrow cells or peripheral blood leukocytes fixed on microscope slides. The reagents were identical to those used in the previous examples.

Preparation of analytes

Nucleated cells (prepared as indicated in Example 1 using either density centrifugation or buffy coats) were deposited on polylysine-coated microscope slides (Sigma), allowed to dry at room temperature, and fixed by treatment with absolute ethanol for 30 minutes. Slides were stored for several weeks at –20° C.

BCR Assay

Slides containing the analyte were treated with horse serum for 30 minutes at room temperature to block nonspecific binding sites, and then treated sequentially with specific monoclonal antibodies, and enzyme-probe covalent conjugate by immersing the slides in the appropriate solutions. Between each treatment, the slides were washed by immersing them for 10 minutes in PBS-BSA.

Typically, the slides were incubated for 30 min at room temperature in a 1:100 dilution of an anticytokeratin 18 IgG1 monoclonal antibody (Sigma), washed twice, incubated for 30 min at room temperature in a dilution 1:500 of the enzyme-probe covalent conjugate, and then washed four times. After the treatment, the slides were placed on a Petri plate and covered with 14 ml of melted soft agar (0.45% Difco heart infusion agar kept at 45° C.) containing penicillin V ($10^5$ units per ml) and $S.$ $lutea$ cells ($10^6$ cells/ml). After overnight incubation at 37° C., bacterial satellite colonies marked the location of tumor cells coated with β-lactamase.

As before, the assay specificity was tested using MCF-7 cancer cells mixed with normal human nucleated cells from either blood or bone marrow. To identify MCF-7 cells, a fluorescein-labeled anticytokeratin 18 IgG1 monoclonal antibody (Sigma) was used as the primary antibody. Results showed that satellite colonies were only present around MCF-7 cells which were easily recognized by their binding fluorescent monoclonal antibody.

EXAMPLE 3

Detection of analytes blotted on nitrocellulose membranes

This example illustrates the use of the invention for detecting extremely small amounts of an analyte present as a blot on a nitrocellulose filter. Reagents were identical to those used in the previous examples.

Serial 1:2 dilutions of a fluorescence-labeled anticyto keratin 18 monoclonal antibody (Sigma) were spotted on a strip of nitrocellulose filter (BA-85; Bio-Rad Ltd.) using a 2-microliter volume for each dilution. The filter was allowed to dry at room temperature for 30 minutes, and then immersed for one hour in 50 ml of a blocking solution (5% skim dry milk in PBS). The strip was removed from the blocking solution, and was covered with a dilution 1:500 of the enzyme-probe covalent conjugate. The strip was allowed to incubate at room temperature for 30 minutes in a covered tray and then washed extensively with PBS-BSA. To visualize the spots, the strip was covered with 14 ml of melted soft agar (0.45% Difco heart infusion agar kept at 45° C.) containing penicillin V ($10^5$ units per ml) and $S.$ $lutea$ cells ($10^6$ cells/ml). After overnight incubation at 37° C., bacterial satellite colonies were observed over most of the spots. The sensitivity of the invention was clearly demonstrated by the fact that spots containing antibody concentrations well below that detectable by fluorescence were nevertheless visualized by the presence of satellite colonies. Control spots lacking the analyte did not show satellite colonies.

EXAMPLE 4

Enumeration of rare tumor cells in human bone marrow or blood specimens

This example illustrates the use of secondary antibody-enzyme complex prepared by the avidin-biotin methodology. As in Example 1, the assay was used to enumerate tumor cells present at extremely low frequency among normal bone marrow cells or peripheral blood leukocytes. The probe was an anticykeratin monoclonal IgM antibody (clone 35βH11) specific for low molecular weight cytokeratin 8 (Dako Corp.).

Preparation of analytes

Nucleated cells were prepared as indicated above (Example 6) using either density centrifugation or buffy coats.

Secondary antibody-enzyme complex

Covalent conjugates were prepared following the procedure described in U.S. Pat. No. 4,002,532, Jan. 11, 1977, hereby incorporated as a reference. Fifty micrograms of streptavidin (Sigma Chemical Co.) were conjugated to 200 micrograms of β-lactamase I (Sigma Chemical Co.) in the presence of 0.005M glutaraldehyde. After 4.5 hours of incubation at room temperature, the reaction mixture was dialyzed extensively against PBS containing 0.1% sodium azide. Bovine serum albumin was added to the conjugate to make a final concentration of 1 mg/ml.

BCR Assay

Suspensions of fixed cells were treated sequentially with anticykeratin 8 monoclonal IgM antibody, biotinylated rabbit anti-mouse IgM immunoglobulin (whole molecule, adsorbed with human serum proteins, Sigma Chemical Co.), and streptavidin-enzyme conjugate. Between each treatment, the cells were washed twice with PBS-BSA. Typically, cells were treated with a dilution 1:50 of the anticytokeratin 8 monoclonal antibody for 30 min at room temperature, separated by centrifugation, and washed with PBS-BSA twice in the same manner. The cellular pellet was resuspended in a dilution (e.g., 1:100) of the rabbit anti-mouse IgM immunoglobulin, and the washing procedure repeated. Finally, the cells were incubated with the streptavidin-enzyme conjugate for 30 min at room temperature. After incubation, the cells were washed four times with PBS-BSA, and then added to 10 ml of melted soft agar (0.45% Difco heart infusion agar kept at 45° C.) containing penicillin V ($10^5$ units/ml) and *S. lutea* cells ($10^6$ cells/ml). After overnight incubation at 37° C., bacterial satellite colonies on the plate were counted using a dissecting microscope or a magnifying lens.

The specificity of the BCR assay was tested as indicated above (Example 1) using MCF-7 tumor cells.

EXAMPLE 5 in situ BCR

A simplified procedure for in situ BCR was developed and performed as follows:

1. A 2-ml sample of peripheral blood (with and without added MCF-7 cells) was mixed with a β-lactamase-antibody conjugate and then incubated for 30 minutes at 37° C. under gentle agitation.
2. After incubation, the blood was diluted with 8 ml PBS-BSA, and filtered by gravity through a coarse Nytex nylon membrane. The cells retained on the membrane were washed rapidly five times with about 1 -ml of PBS-BSA each time. This step takes 2–3 minutes.
3. Immediately after the last wash, the cells were transferred to a glass slide coated with polylysine ("Polyprep" slide, Sigma Chemicals) by putting the membrane (cells down) on the slide for about 3 minutes. This cell transfer is quantitative because cells do not bind the negatively charged Nytex membrane while attaching readily to the positively charged Polyprep slide. By staining the Nytex membranes after cell transfer it was ascertained that no detectable cells remained attached to the membrane.
4. The slide was placed in contact with an agar film containing *S. lutea* and penicillin V, and incubated overnight at 37° C. in a humidified box.
5. The satellite colonies were then enumerated. The presence of MCF-7 cells was ascertained using a duplicate set of slides (after Step 3) on which cells were fixed and stained for cytokeratin 18 using a Dako APAAP KIT™ for immunocytochemistry.

EXAMPLE 6

Comparison of enzymes potentially useful in BCR

Selection of an enzyme to act on the regulatory substrate in the BCR can significantly affect a variety of properties of the assay. This example compares the benefits of two enzymes, β-galactosidase and β-lactamase I, for use in the BCR.

Minimizing false positives

In contrast to β-galactosidase, β-lactamase I is not found in eukaryotic cells. Using β-lactamase I, therefore, circumvents the potential problem of false positives due to cells with endogenous β-galactosidase.

Enzyme activity

The catalytic activity of β-lactamase I ranks among the highest known values approaching that of diffusion-limited reactions, and its turnover number ($1 \times 10^5$ to $1 \times 10^6$ min$^{-1}$) is comparable to that of peroxidase.

Preparation of the multifunctional probe

β-lactamase I is more amenable than β-galactosidase to chemical modifications because β-lactamase I is a monomer of 30,800 daltons while β-galactosidase is a tetramer of 465,000 daltons. In addition, β-lactamase I has a high content of lysine and arginine, no cystein residues, good thermal stability, and binds to solid phases without loss of activity.

Use of enzyme with proliferating cells

In contrast to the galactosidase-based BCR requiring a particular riboflavin-deficient *E. coli* mutant, the lactamase-based system can be performed with many different bacteria species since the only requisite is for bacteria to be sensitive to a β-lactam antibiotic. Bacterial spores are also suitable for the lactamase-based BCR and may offer advantages over vegetative cells.

EXAMPLE 7

Assays for the optimization of BCR

Reaction matrix conditions may sometimes be optimized empirically. To facilitate the initial process of optimizing a particular BCR system, simple analyte-multifunctional probe complex substitutes may be used.

In one embodiment, the analyte substitute consisted of small pieces (1-cm long) of ordinary cotton thread soaked with graded concentrations of β-lactamase I. The end-point was the lowest enzyme concentration yielding bacterial microcolonies around the thread. The reproducibility of the method was tested by measuring the radioactivity of individual threads soaked with a radioactive solution. The results showed that the average amount of radioactive solution retained by individual threads was 3,452 CPM (equivalent to 1.01 μl volume) with a standard error of the mean of ±12%.

Another analyte substitute was designed to mimic enzymatic activity of β-lactamase-coated MCF-7 cells. The analyte consisted of biotin-coated acrylic beads (50μ diameter, Sigma Chemical Corp.) coupled to a streptavidin-β-lactamase covalent conjugate. The covalent conjugate was prepared using glutaraldehyde as multifunctional coupling agent. After treatment, the beads were washed extensively with PBS-BSA to eliminate unbound enzyme, and then stored at 0°–4° C. For testing, individual beads were deposited (using a sterile Pasteur pipette) on the surface of agar films containing bacteria and penicillin. Semi-quantitative measurements of sensitivity were obtained by measuring the diameter of satellite colonies around individual beads. Because of their uniformity and stability under storage, these beads provided a valuable tool for optimizing the BCR under standard conditions.

EXAMPLE 8

Sensitivity studies

Diffusion

One element of sensitivity in the BCR is the rate of alteration of the regulatory substrate to the growth promoting/permitting state. Under the assay conditions, enzyme activity in most cases will be at least partially limited by diffusion of the regulatory substrate towards the analyte. Two ways in which diffusion of the regulatory substrate may be accelerated are by decreasing the hydrogel concentration and/or increasing the concentration of the regulatory substrate itself.

In the case where penicillin is to be used as the regulatory substrate it is important that a rate of penicillin hydrolysis high enough to lower the penicillin concentration from $C_i$, the initial concentration present in the agar, to $C_g$, a critical concentration that triggers bacterial growth near the analyte is achieved. Consistent with this premise, it was observed that increasing the diffusion rate of penicillin in the agar increased the assay sensitivity. Changes in diffusion rate were effected by changing the agar concentration or by using purified agar or agarose solidifying at a lower concentration than ordinary bacteriological agar.

Another means to increase assay sensitivity is to decrease the reaction volume in which enzyme activity occurs. Reducing the reaction volume diminishes the critical absolute amount of altered regulatory substrate which is equal to $v (C_i-C_g)$; where v is the reaction volume. The validity of this hypothesis was tested by comparing the sensitivity of assays in which agar films of different thickness were used as the reaction matrix. Penicillin and β-lactamase I were used as the growth regulatory system. A sensitivity increase of about 2-fold was observed when the agar thickness was reduced from 4 to 1 mm.

Bacterial Concentration

In general, optimal assay sensitivity was achieved at concentrations of about $5 \times 10^5$ bacteria/ml. In experiments with *E. coli*, it was noticed that the minimal penicillin concentration that completely inhibited growth was roughly proportional to the number of bacteria per ml. In contrast, for *S. lutea* it was found that penicillin inhibited growth independently of bacterial concentration.

Chemical composition of the growth medium

During preliminary experiments, four growth media were tested, including a simple inorganic medium (Davis minimal medium) and three complex media from Difco, Antibiotic Medium No. 3, Heart Infusion Broth, and Nutrient Agar. Using *E. coli*, it was found that the complex media were superior to inorganic medium, but there was no significant difference between the three complex media. In contrast, for *S. lutea*, Heart Infusion Broth was better than the other media. An important observation in this series of experiments was that *S. lutea* grew well in Antibiotic Medium No. 3 but the sensitivity of the BCR was reduced. Since Antibiotic Medium No. 3 contains more inorganic salts than Heart Infusion Broth, we tested Antibiotic Medium No. 1, a salt-free formulation of Antibiotic Medium No. 3. A 2-fold increase in sensitivity was observed using the salt-free medium.

EXAMPLE 9

BCR kit & method

The components and operating procedures of an assay kit for detecting occult micrometastasis in clinical specimens of bone marrow peripheral blood is described below.

Equipment required: 1) Incubator for 37° C.; 2) Magnifying glass or dissecting microscope.

Optional equipment: 1) Cytospin adapters for conventional centrifuges, or a Cytocentrifuge.

Materials and Reagents
1. Microscope slides coated with an appropriate substance (e.g., poly-L-lysine) to facilitate cell adhesion (several types of these slides are commercially available from Sigma, Fisher Scientific, and other suppliers).
2. Reaction matrix containing nutrients, penicillin and bacteria immobilized on a polymer film.
3. Soluble multifunctional probe containing lactamase, mouse IgG anti-lactamase, anti-cytokeratin monoclonal IgG, and a crosslinking antibody (e.g., immunoglobulin fraction of rabbit antiserum to mouse IgG).
4. Buffer solutions and for quenching solution for rinsing (e.g., PBS-BSA, powdered milk).

Assay Procedure

Perform all incubations at room temperature

Step 1. Separate nucleated cells from the specimen using Ficoll-Hypaque density gradient centrifugation.

Step 2. Smear (or cytospin) the nucleated cells on several slides using about $5 \times 10^5$ cells/slide. Air-dry for 2 hours or overnight. Immerse the slides in absolute ethanol for 1–2 min to fix the cells. The slides may be stored at –20° C. or lower. Wrap the slides airtight if they are to be stored.

Step 3. Apply blotting solution to the slides and incubate for 10 min. Remove excess solution.

Step 4. Apply the lactamase immune complex and incubate for 30 min. Rinse gently with buffer from a wash bottle removing excess of liquid, and then place the slides in a buffer bath for 5–20 min.

Step 5. Peel off the protective wrap from the reaction matrix with bacteria, and place the slides (cells down) on top of the film. Ascertain that no air bubbles are trapped between the slide and the film surface. Incubate the film overnight at 37° C.

Step 6. Examine the slides under a magnifying glass or a dissecting microscope, and mark the location of galaxy colonies using a glass marking pen or a diamond marker (if an organic solvent is to be used for subsequent staining).

Step 7. Stain the cells using the chromogenic substrate for β-lactamase.

What is claimed is:

1. A method for determining an analyte in a sample comprising the steps of:

(a) providing the sample;

(b) contacting the sample with a probe comprising an enzyme conjugated to a specific binder which specifically binds to the analyte to form a probe-analyte complex if said analyte is present, wherein said enzyme is capable of degrading a preselected bacterial growth inhibitory substance;

(c) removing unbound probe from the sample comprising said probe-analyte complex;

(d) contacting the complex of step (c) with a homogeneous reaction layer comprising a matrix comprising (i) a sample of bacterial cells whose growth is inhibited by said growth inhibitory substance, (ii) a complete growth medium in an amount sufficient to promote proliferative growth of said bacterial cells, and (iii) said growth inhibitory substance in an amount sufficient to reduce said proliferative growth of said bacterial cells, to produce an assay system;

(e) incubating said assay system of step (d) for a time sufficient for said enzyme to degrade said growth inhibitory substance, thereby providing enhanced growth of said bacterial cells in regions where said growth inhibitory substance has been degraded; and, (f) determining said analyte by correlating the presence or amount of said enhanced growth regions, as compared to a background region where said growth inhibitory substance has not been degraded, to the presence or amount of said analyte in said sample.

2. The method of claim 1 wherein the analyte is a surface antigen present on a preselected target cell.

3. The method of claim 1 wherein the analyte is an intracellular antigen present in a preselected target cell and said target cell is permeabilized prior to contacting said sample with said probe.

4. The method of claim 3 wherein said intracellular antigen is a nucleic acid.

5. The method of claim 3 wherein said intracellular antigen is a protein.

6. The method of claim 1 wherein said method further comprises the step of fixing said sample to an immunoblot or dot blot solid phase prior to contacting said sample with said probe.

7. The method of claim 1 wherein said analyte is a tumor marker for mammalian tumor cells.

8. The method of claim 1 wherein said enzyme is selected from the group consisting of β-lactamase, β-galactosidase, glucosidase, esterase, acetyltransferase, adenyltransferase, adenosine deaminase, penicillinase, nucleosidase, and phosphotransferase.

9. The method of claim 1 wherein said growth inhibitory substance is an antibiotic selected from the group consisting of cephalosporin, chloramphenicol, kanamycin, formycin, penicillin, puromycin, streptomycin, and gentamicin.

10. The method of claim 1 wherein said sample is blood or bone marrow.

11. The method of claim 10 wherein said bacterial cells are selected from the group consisting of *Bacillus subtiliis, Bacillus cereus, Escherichia cloacae, Providencia stuartii, Psuedomonas aeruginosa, Serratia marcensens, Sarcina lutea, Vibrio fischeri, Escherichia coli* and *Staphylococcus aureus.*

12. The method of claim 1 wherein said specific binder is an antibody or an immnunoreactive fragment thereof.

13. The method of claim 1 wherein the analyte is cytokeratin and the specific binder is an anticytokeratin antibody or an immunoreactive fragment thereof.

14. The method of claim 1 wherein the analyte is a nucleic acid and the specific binder is a nucleotide sequence complementary to said nucleic acid.

15. The method of claim 1 wherein said bacterial cells are luminescent and said determining step further comprises applying a light sensitive film to said reaction layer of step (e) for a time sufficient for said luminescent bacterial cells to expose said film.

16. A kit for the detection of an analyte in a sample said kit comprising:

(a) a probe comprising an enzyme conjugated to a specific binder which specifically binds to said analyte to form a probe-analyte complex, wherein said enzyme is capable of degrading a preselected bacterial growth inhibitory substance;

(b) a sample holding means capable of receiving said sample and said probe;

(c) a homogeneous reaction matrix comprising (i) a hydrogel, (ii) a sample of bacterial cells whose growth is inhibited by said growth inhibitory substance, (iii) a complete growth medium in an amount sufficient to promote proliferative growth of said bacterial cells, and (iv) said growth inhibitory substance in an amount sufficient to reduce said proliferative growth of said bacterial cells, wherein said reaction matrix is fixed to a backing material.

17. The kit of claim 16 further comprising an immunoblot or dot blot solid phase.

\* \* \* \* \*